United States Patent
Tran (12) United States Patent (10) Patent No.: US 7,232,798 B2
(45) Date of Patent: Jun. 19, 2007

(54) NEUROPROTECTION AND NEUROEGENISIS BY ADMINISTERING CYCLIC PROLYL GLYCINE

(76) Inventor: Loi H. Tran, 5212 Deepdale Way, Elk Grove, CA (US) 95758

( * ) Notice: Subject to any disclaimer, the term of this patent is extended or adjusted under 35 U.S.C. 154(b) by 0 days.

(21) Appl. No.: 10/292,732

(22) Filed: Nov. 12, 2002

(65) Prior Publication Data

US 2003/0109531 A1     Jun. 12, 2003

Related U.S. Application Data

(60) Provisional application No. 60/405,909, filed on Aug. 26, 2002.

(30) Foreign Application Priority Data

Nov. 13, 2001   (NZ)  ................................ 515432

(51) Int. Cl.
*A61K 38/12*     (2006.01)
*A61K 38/05*     (2006.01)

(52) U.S. Cl. .................. 514/9; 514/2; 514/11
(58) Field of Classification Search .......... 514/9, 514/11, 10, 249, 2
See application file for complete search history.

(56) References Cited

U.S. PATENT DOCUMENTS

| | | | | |
|---|---|---|---|---|
| 5,439,930 A | * | 8/1995 | Seredenin et al. | .......... 514/423 |
| 6,124,361 A | * | 9/2000 | Chenard | ............. 514/561 |
| 6,187,906 B1 | * | 2/2001 | Gluckman et al. | .......... 530/331 |
| 6,251,865 B1 | | 6/2001 | Clark | |
| 6,258,582 B1 | | 7/2001 | Acton | |
| 6,284,778 B1 | | 9/2001 | Zelle | |
| 6,291,213 B1 | | 9/2001 | Rothstein | |
| 6,291,511 B1 | | 9/2001 | Durette | |
| 6,303,576 B1 | | 10/2001 | Blaschuk et al. | |
| 6,689,904 B2 | * | 2/2004 | Greenfield et al. | .......... 562/499 |
| 2003/0109531 A1 | | 6/2003 | Tran | |

FOREIGN PATENT DOCUMENTS

| | | | |
|---|---|---|---|
| EP | 0366638 A2 | * | 2/1990 |
| EP | 0363994 | * | 4/1990 |

(Continued)

OTHER PUBLICATIONS

Gangemi et al., Regulatory genes controlling cell fate choice in embryonic and adult neural stem cells, Journal of Neurochemistry, 2004, vol. 89, pp. 286-306.*

(Continued)

*Primary Examiner*—Mark L. Shibuya
(74) *Attorney, Agent, or Firm*—David R. Preston & Associates APC; David Preston (57) ABSTRACT

The invention relates to the use of cyclic Prolyl Glycine ("cyclic PG" or "cPG") and analogs and mimetics thereof, as neuroprotective agents for the treatment and or prevention of neurological disorders including but not limited to cerebral ischemia or cerebral infarction resulting from a range of phenomena, such as thromboembolic or hemorrhagic stroke, cerebral basospasms, hypoglycemia, cardiac arrest, status epilepticus, perinatal asphyxia, anoxia such as from drowning, pulmonary surgery, and cerebral trauma, as well as to the treatment and prevention of chronic neurodegenerative disorders such as Alzheimer's disease, Parkinson's disease, and Huntington's disease, and as anticonvulsants.

8 Claims, 5 Drawing Sheets

FOREIGN PATENT DOCUMENTS

| | | |
|---|---|---|
| NZ | 515371 | 11/2001 |
| NZ | 515432 | 11/2001 |
| WO | WO 9302695 A1 * | 2/1993 |
| WO | WO99/47490 * | 9/1999 |
| WO | 03/039487 A2 | 5/2003 |
| WO | 03/039487 A3 | 5/2003 |
| WO | 03/041655 A2 | 5/2003 |

OTHER PUBLICATIONS

Liu et al., cAMP, tubulin, axonal transport and generation, Experimental Neurology, vol. 189, (2004), pp. 199-203.*
Bhargava et al., Neuropharmacology, vol. 21, pp. 917-922, 1982.*
Gudasheva et al., European Journal of Drug Metabolism and Pharmacokinetics 1997, vol. 22, No. 3, pp. 245-252.*

* cited by examiner

Theoretical Binding of GP with IGF-I Binding Protein

M: Metal ions i.e. Ca2+, Mg 2+ by Loi H Tran

Effects of cPG on functonal recovery after 6-OHDA lesion

NEUROPROTECTION AND NEUROEGENISIS BY ADMINISTERING CYCLIC PROLYL GLYCINE

CROSS-REFERENCE TO RELATED APPLICATIONS

This application claims benefit of priority to New Zealand provisional patent No. 515432 filed Nov. 13, 2001, and U.S. provisional patent application Ser. No. 60/405,909 filed Aug. 26, 2002, and both incorporated by reference herein.

BACKGROUND OF THE INVENTION

NMDA AMPA Receptors

Excessive excitation by neurotransmitters can cause the degeneration and death of neurons. It is believed that this degeneration is in part mediated by the excitotoxic actions of the excitotoxic amino acids (EAA) glutamate and aspartate at the N-methyl-D-aspartate (NMDA) receptor, the alpha-amino-3-hydroxy-5-methyl 4-isoxazole proprionic acid (AMPA) receptor, and the kainate receptor. AMPA/Kainate receptors may be referred to jointly as non-NMDA receptors.

This excitotoxic action is considered responsible for the loss of neurons in cerebrovascular disorders such as cerebral ischemia or cerebral infarction resulting from a range of conditions, such as thromboembol or hemorrhagic stroke, cerebral vasospasm, hypoglycemia, cardiac drowning, pulmonary surgery, and cerebral trauma, as well as Alzheimer's disease, Parkinson's disease, and Huntington's disease.

Among excitatory amino acid receptor antagonists recognized for usefulness in the treatment of neurological disorders are those that block AMPA receptors. (Bigge C. F. and Malone T. C., Curr. Opin. Ther. Pat., 1993:951; Rogawski M. A. TiPs, 1993; 14: 325).

AMPA receptor antagonists have prevented neuronal injury in several models of global cerebral ischemia. (Li H. and Buchan A. M., J. Cerer. Blood Flow Metab., 1993; 13: 933; Nellga B. and Wielock T. J. Cerer. Blood Flow Metab., 1992; 12:2) and focal cerebral ischemia (Bullock R., Graham D. I. Swanson S., McCullock., J. Cerer. Blood Flow Metab. 1994; 14: 466; Xue D. et al J. Cerer. Blood Flow Metab., 1994; 14: 251).

AMPA receptor antagonists have also demonstrated promise in chronic neurodegenerative disorders such as Parkinson's disease. (Klockgether T. et al., Ann. Neurol., 1993; 34 (4): 585-593).

Excitatory amino acid receptor antagonists that block NMDA receptors are also recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include cerebral ischemia (stroke or cerebral trauma, for example), muscular spasm, convulsive disorders, neuropathic pain, and anxiety, and may be a significant causal factor in chronic neurodegenerative disorders such as Parkinson's disease (Klockgether T., Turski L., Ann. Neurol. 1993; 34: 585-593), human immunodeficiency virus (HIV) related neuronal injury, amyotrophic lateral sclerosis (ALS); Alzheimer's disease (Francis P. T, et al. J. Neurochem. 1993; 60(5): 1589-1604) and Huntington's Disease (Lipton S., TINs, 1993; 16(12): 527-532; Lipton S., Rosenberg P. A. New Eng. J. Med 1994; 330 (9): 613-622); Bigge C. F. Biochem. Pharmacol. 1993; 45: 1547-156).

NMDA receptor antagonists may also be used to prevent tolerance to opiate analgesisa or to help control withdrawal symptoms from addictive drugs.

A Novel Antagonist to NMDA/AMPA

This invention relates to the discovery of the functions of cyclic Propyl Glycine (herein referred to as "cyclic PG" or "cPG") as a novel antagonist that either blocks the AMPA and/or the NMDA receptors.

CPG has been found to be an endogenous compound exhibiting anxiolytic activities in animal studies by Gudasheva T. A et al (Biull Eksp Biol Med 1999 October 128:10 411-3) and Seredenin S. B. et al (Bull Exp Biol Med 2002 April 133:360-2).

We have surprisingly discovered that cPG is the end product of the metabolites of glycine-proline-glutamate (GPE), which in turn is one of the components of the cleavage of insulin-like growth factor I (IGF-I).

IGF-I is a 70 amino acid-long polypeptide with several metabolic actions known to be expressed in the rat brain during development and after acute injury. (D'Ercole, A J et al Molecular Neurobiology 1996; 13: 227-255).

Some of the biological effects of IGF-I are probably facilitated by des (1-3) IGF-I, an IGF-I derivative lacking the N-terminal tripeptide glycine-proline-glutamate (GPE). It was reported that des (1-3) IGF-I is less effective than recombinant human IGF-I (nhIGF-I) as a neuronal rescue agent, which suggests that the central effect of IGF-I might be partially mediated by the tripeptide GPE. (Guan J, et al Endocrinology 1996; 137: 893-898).

However, it was Sara et al, who in 1989 showed that GPE is a neuroactive peptide which facilitates the release of both acetylcholine and dopamine from cortical slices in vitro. (Biochem. Biophys. Res. Comn 1989; 165: 766-771).

Sarah's group has Swedish, European, and Japanese patents on GPE as a neuromodulatory peptide (EP0366638, SE8803847, JP2250895).

The US patent by Bourguignon et al, U.S. Pat. No. 5,804,550 or W094/26301 suggests that GPE is an NMDA antagonist.

The US patent by Gluckman et al, U.S. Pat. No. 6,187,906 claims that GPE can be used to protect dopaminergic neurons of a mammal against death from Parkinson's disease. This group reported that the mechanism by which GPE leads to prevention of cell death was not known, but was not by modulating neuronal activity.

In their patent claims, the Gluckman group proposed that the "concentration of GPE and/or analogues thereof in the CNS and in the brain of the patient in particular should be increased in order to treat the CNS damage." They also proposed a suitable dosage range to be between about 0.1 to 1,000 μg of GPE per 100 g of body weight where the composition is administered centrally.

However, the Gluckman patent (filed on Jul. 15, 1999 and issued on Feb. 13, 2001) did not cite a publication by Curatolo L. et al (Annals of New York Academy of Sciences 1995; 765: 145-150 *Neuroprotective effect of GPE Pretreatment on rat Hippocampal Organotypic cultures exposed to NMDA*), in which the effect of GPE did not seem to be clearly concentration-dependent. The highest degree of neuroprotection was obtained with 10 μM GPE while lower (1 μM) or higher (50-100 μM) concentrations reduced the neuronal damage to a lesser extent. The lack of a concentration-dependent effect does not indicate a single receptor-mediated effect. In fact, the bell-shaped curve describing the pharmacological effect of increasing concentrations of GPE might be the result of multiple mechanisms of action.

Without the clear understanding of the mechanism of action of GPE, it was very difficult to determine the optimal dosage or human treatment. The empirical bell-shaped curve-model for rats may be only applied to rats and might not be entirely appropriate for human applications.

Private communication with the Gluckman group showed unpublished results of recent studies in which high concentrations of GPE administered intraperitoneally and intravenously caused severe brain damage to rats. It was questionable whether GPE may be a suitable neuroprotective agent based on unreproducible results of the bell-shaped curve concentrations of GPE.

The uncertainty of the concentration dependency was not only observed in GPE, but also with IGF-I. Johnston B. et al (J. Clini. Invest. Volume 97, Number 2, January 1996, pp 300-308 and subsequent private communications) reported that 1 µg IGF-I is more neuroprotective than 100 ng in fetal sheep studies, but when the dose increased from 1 µg to 10 µg all the neuroprotective effects are lost. It was found that increasing the dose to 100 µg or more usually killed the sheep fetus. It was not known why the neuroprotective dose in the fetal sheep (weighs about 3.5 kg) was about 500 times less than the effective dose in the rat (weighs about 350 g) if the difference in weight between the fetus and rat is taken into account (a fetal sheep weighs about 10 times the rat).

The present invention provides an explanation to the unpredictable bell-shaped curve effect of the concentrations of IGF-I and GPE. The present invention provides a novel mechanism of action of GPE, in which GPE is not a final product of the cleavage of IGF-I, but GPE is metabolized into cyclic Propyl Glycine and glutamic acid, as illustrated in FIG. 1.

Over the past twenty years there have been a large number of publications reporting the neurological effects of the insulin like growth factors. (Pimentel E. (1994) Handbook of Growth Factors, Volume 1-3, CRC Press (Ann Arbor). Now with the finding that IGF-1 and GPE are the pro-drug of cPG, we now can link the biological activities of these pro-drugs to cPG, thus not only enabling us to study the mechanisms of action of IGF-1 and GPE, but also to attribute the neuroprotective activities of these two compounds to cPG and their neurotoxicity to the corresponding glutamic acids.

It is noted that the stereoisomers of GPE are important factors and it is found that only the cis form of GPE can be metabolized into cyclic Propyl Glycine and glutamic acid. Since glutamic acid or glutamate is a well-known neurotoxic agent, it is predicted that cyclic Propyl Glycine (cPG) must possess very potent neuroprotective effect to overcome the intrinsic neurotoxicity of glutamate.

Figure 1:
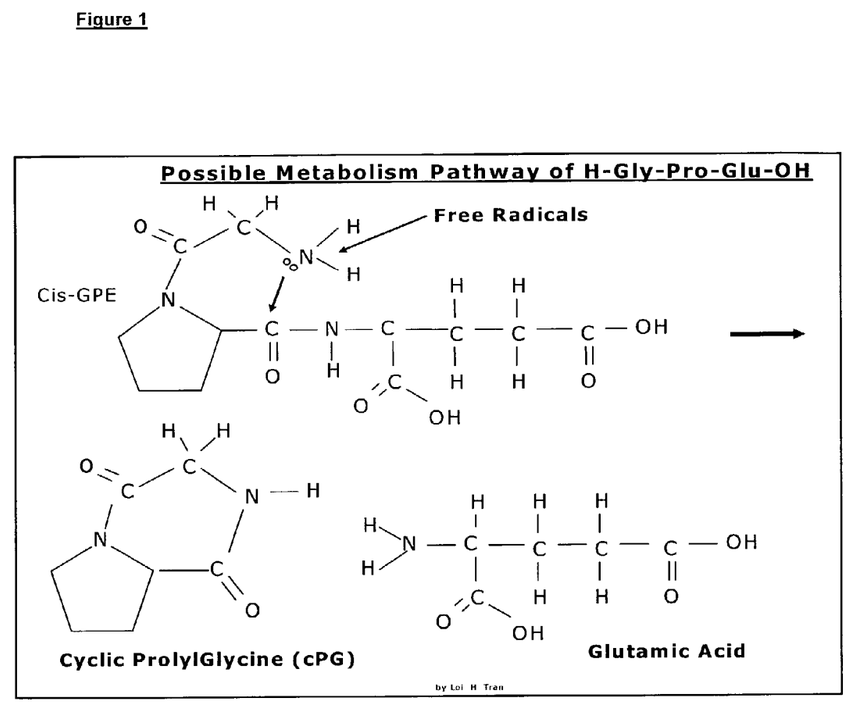
FIG. 1 illustrates the proposed metabolism pathway of cis-GPE to cyclic Prolyl Glycine and glutamic acid.
Figure 2:
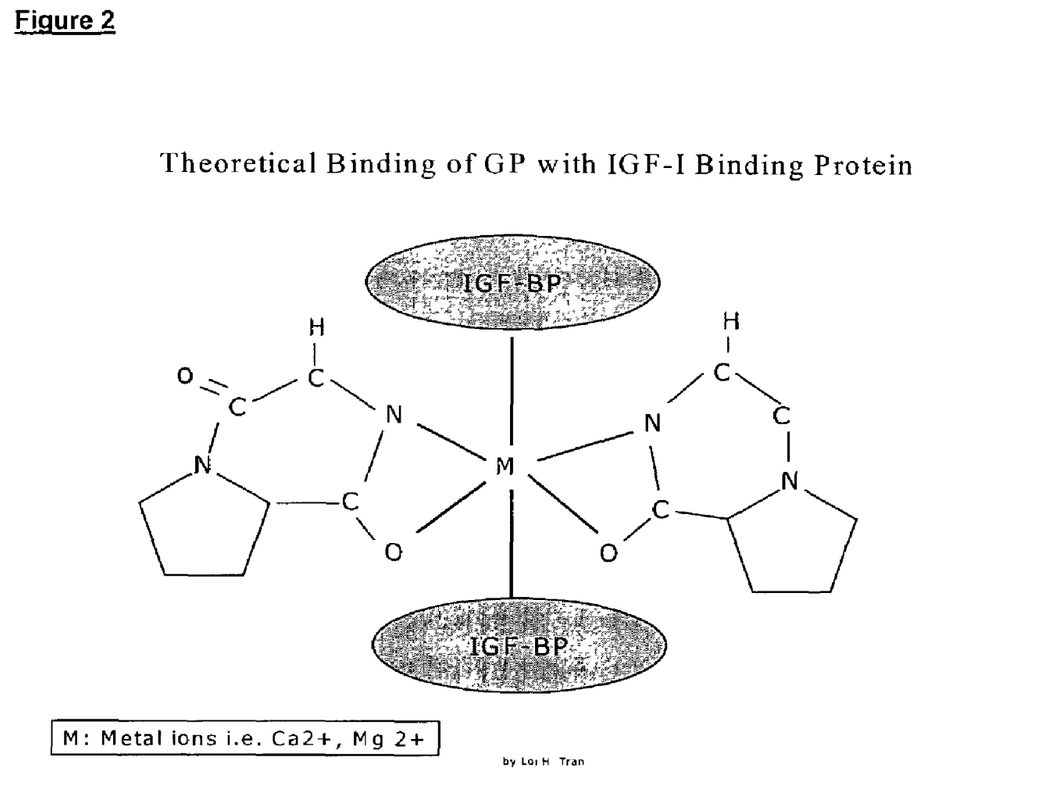
FIG. 2 illustrates the proposed mechanism by which cyclic prolyl glycine may act to bind metal ions.

As shown in the FIGS. 1 and 2, cyclic PG can form chelating complexation with metal ions such as calcium ions, magnesium ions, and it also can bind to large molecules such as IGF-Binding Proteins, such that cyclic PG can serve as a neurotransmittance agent or a neurotransportor as well as an energy storage in the central nervous system. These attributes can make cyclic PG an anti-necrotic and anti-apoptotic agent in the central nervous system.

Our experimental results reported herein, serving as limited examples, showed that cPG not only acts as a potent neuroprotective agent but also serves as a neurogenesis agent, which can be considered a novel drug candidate for treatment of neurological disorders.

SUMMARY OF THE INVENTION

One aspect the invention provides cyclic Prolyl Glycine compounds suitable for the treatment or prevention of disease and injury in animals and humans. The cyclic PG being selected from the group that includes cPG, cPG analogues, cPG pepticlomimetrics and relating compounds which promote or cause the formation of cPG or cPG analogues in vivo.

Preferably the cPG compounds are administered in a pharmaceutically acceptable composition.

More preferably the composition additionally includes a therapeutic amount of a cPG compound in combination with a compound selected from growth factors and associated derivatives (insulin-like growth factor-I [IGF-I], insulin-like growth factor-II [IGF-II], GPE, transforming growth factor-ill, activin, growth hormone, nerve growth factor, growth hormone binding protein, JQF-binding proteins [especially JGFBP-3], basic fibroblast growth factor, acidic fibroblast growth factor, the hst/Kfgk gene product, FGF-3, FGF-4, FGF-6, keratinocyte growth factor, androgen-induced growth factor. Additional members of the FGF family include, for example, int-2, fibroblast growth factor homologous factor-1 (FHF-1) FHF-2 FHF-3 and FHF-4, karatinocyte growth factor 2, glial-activating factor, FGF-10 and FGF-16, ciliary neurotrophic factor, brain derived growth factor, neurotrophin 3, neurotrophin 4, bone morphogenetic protein 2 [BMP-2], glial-cell line derived neurotrophic factor, activity-dependant neurotrophic factor, cytokine leukaemia inhibiting factor, oncostatin M, interleukin), $\beta,\alpha,\chi$ or consensus interferon, TNF-$\alpha$; clomethiazole; kynurenic acid, Semax, FK506 [tacrolimus], L-threo-1-pheyl-2-decanoylamino-3-morpholino-1-propanol, andrenocorticotropin-(4-9_analogue [ORG2766] and dizolcipine [MK-801], selegiline; glutamate antagonists such as, NPS15O6, GV1505260, MK-801, GV150526; AMPA antagonists such as 2,3-dihydroxy-6-nitro-7-sulfamoylbenzo(f)quinoxaline (NBQX), LY303070 and LY300164; anti-inflammatory agents directed against the addressin MAdCAM-1 and/or it integrin $\alpha 4$ receptors ($\alpha 4\beta 1$ and $\alpha 4\beta 7$), such as anti-MAd-CAM-11mAb MECA-367 (ATCC accession no. (HB-9478), interferons including interferon beta 1b and interferon alfa-con-1.

Preferably the cPG compounds may be used in the treatment or prevention of cell damage or cell death in response to diseases and injury resulting from septic shock, ischemia, administration of cytokines, overexpression of cytokines, ulcers, gastritis, ulcerative colitis, Crohn's disease, diabetes, rheumatoid arthritis, asthma, Alzheimer's disease, Parkinson's disease, multiple sclerosis, stroke, cirrhosis, allograft rejection, transplant rejection, encephalomyelitis, meningitis, pancreatitis, peritonitis, vasculitis, lymphocytic choriomeningitis glomerulonephritis, uveitis, glaucoma, blepharitis, chalazion, allergic eye disease, corneal ulcer, keratitis, cataract, retinal disorders, age-related macular degeneration, optic neuritis ileitis, inflammation induced by overproduction of inflammatory cytokines, hemorrhagic shock, anaphylactic shock, bum, infection leading to the overproduction of inflammatory cytokines induced by bacteria, virus, fungus, and parasites, hemodialysis, chronic fatigue syndrome, stroke, cancers, cardiovascular diseases associated with overproduction of inflammatory cytokines, heart disease, cardiopulmonary bypass, ischemic/reperfusion injury, ischemic/reperfusion associated with overproduction of inflammatory cytokines, toxic shock syndrome, adult respiratory distress syndrome, cachexia, myocarditis, autoimmune disorders, eczema, psoriasis, heart failure, dermatitis, urticaria, cerebral ischemia, systemic lupus erythematosis, AIDS, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Huntington's disease, epilepsy, gastrointestinal motility disorders, obesity, hyperphagia, neuroblastoma, malaria, hematologic cancers, myelofibrosis, lung injury, graft-versus-host disease, head injury, CNS trauma, hepatitis, renal failure, chronic hepatitis C, paraquat poisoning, transplant rejection and preservation, fertility enhancement, bacterial translocation, circulatory shock, traumatic shock, hemodialysis, hangover, and combinations of two or more thereof.

Preferably the cPG compounds may be used in the restoration of myelination of axons in mammals where myelin depleted due to neural injury or disease.

Preferably cPG compound may be used in the restoration of myelination where depletion due to trauma, toxin exposure, asphyxia or hypoxia-ischemia, perinatal hypoxic-ischemic injury, injury to or disease of the white matter of the CNS, acute brain injury, chronic neurodegenerative disease including multiple sclerosis, and demyelinating diseases and disorders including acute disseminated encephalomyelitis, optic neuritis, transverse myelitis, Devic's disease, the leucodystrophies; non-inflammatory involvement; progressive multifocal leukoencephalopathy, and central pontine myelinolysis.

Preferably the cPG compound will be administered in combination with IGF-1 or an interferon.

Another related aspect the invention relates to a method of treating or preventing cell damage or cell death in response to injury and disease by administering at least one cPG compound.

Preferably the cPG compound will be administered at between about 1 μg to about 150 mg per kilogram of bodyweight. A suitable dosage for administration of cPG may be, for example, at between 0.1 mg to about 100 mg per kilogram of body weight, at between about 1 mg to about 75 mg per kilogram of body weight, at between 10 mg to about 50 mg per kilogram of body weight, or at between about 20 mg to about 40 mg per kilogram of bodyweight.

A further aspect the invention relates to a method of restoring the myelination of axons in a mammal in need of restored myelination due to neural injury or disease, comprising administering a therapeutic amount of a cPG compound, where a cPG compound comprises cPG, a biologically active cPG analogue, a biologically active cPG peptidomimetic, a compound that increases the concentration of cPG, or a compound that increases the concentration of cPG analogues, effective to restore myelination of axons in a mammal. In one aspect of the invention, the method of restoring myelination of axons comprising administering a therapeutic amount of a cPG compound comprises stimulation of astrocytes to promote remyelination. In another aspect of the invention, the method of restoring myelination of axons comprising administering a therapeutic amount of a cPG compound comprises stimulation of oligodendrocytes to produce myelin.

In yet another aspect of the invention, the method of restoring myelination of axons to a mammal in need of restored myelination further comprises administering a therapeutic amount of a cPG compound in combination with a compound selected from IGF-I or an interferon. In one aspect of the invention, the method of restoring myelination of axons comprising administering a therapeutic amount of a cPG compound in combination with IGF-I or an interferon to stimulate astrocytes to promote remyelination. In another aspect of the invention, the method of restoring myelination of axons comprising administering a therapeutic amount of cPG in combination with IGF-I or an interferon to stimulate oligodendrocytes to produce myelin. In preferred embodiments, the interferon comprises interferon beta 1b (Betaseron). In a further most preferred embodiment, the interferon comprises consensus interferon (Infergen®, interferon alfa-con-1).

In still a further aspect of the invention, the methods to treat or prevent cell damage and death in response to injury and disease, comprises administration of a therapeutic amount of a cPG compound in an amount from about 1 μg to about 150 mg of cPG per kg of body weight of the mammal.

In yet another aspect of the invention, the method of restoring myelination of axons to a mammal in need of restored myelination further comprises administering a therapeutic amount of a cPG compound in combination with IGF-1 from about 1 to 10 mg of IGF-I per 1 Kg body weight of the mammal or an interferon from about 0.1 to 1000 μg of IGF-I per 100 g of body weight of the mammal. In a preferred embodiment, the interferon is interferon beta. In the most preferred embodiment, the interferon is interferon beta 1b (Betaseron). In a further most preferred embodiment, the interferon comprises consensus interferon (Invergen®, interferon alfacon-1).

In a further preferred embodiment of the methods to treat or prevent cell damage and death in response to injury and disease, comprising administration of a cPG compound, the cPG compound is administered to the mammal through a shunt into a ventricle of the mammal.

In a further preferred embodiment of the methods to treat or prevent cell damage and death in response to injury and disease, comprising administration of a cPG compound, the cPG compound is administered to the mammal by peripheral administration.

The present invention provides a method of treatment for stimulating mature astrocytes to promote myelin production after hypoxic-ischemic injury including the step of increasing the active concentration of cPG and/or the concentration of analogues of cPG in the CNS of mammals.

Most preferably, it is the effective amount of IGF-I itself that is increased within the CNS of the mammal. This can be effected by direct administration of cPG and indeed this is preferred. However, the administration of compounds that indirectly increase the effective amount of IGF-I (for example a pro-drug which, within the patient is cleaved to release cPG) is in no way excluded.

The active compound (IGF-I or its analogue or its mimetic) can be administered alone, or as is preferred, a part of a pharmaceutical composition.

The composition can be administered directly to the CNS. The latter route of administration can involve, for example, lateral cerebro-ventricular injection, focal injection or a surgically inserted shunt into the lateral cerbro-ventricle of the brain of the patient. The composition can be administered in combination with an artificial cerebrospinal fluid.

Conveniently, the stimulation and promotion of myelin production in oligodendrocytes and the support, stimulation and promotion of remyelination by mature astrocytes is promoted through the administration of cPG compounds in the prophylaxis or therapy of demyelinating diseases such as multiple sclerosis.

BRIEF DESCRIPTION OF DRAWINGS

A better understanding of the invention will be gained from reference to the following examples and drawings wherein.

DETAILED DESCRIPTION OF THE INVENTION

The following examples are given by way of illustration only and shall not be taken as limiting the scope of the invention.

It has been surprisingly discovered that the process of the metabolism of IGF1 to the tripeptide GPE and des IGF is only a part of the process.

The cis-isomer of the GPE can further break down to form a cyclic Prolyl Glycine and glutamic acid. This is shown in FIG. 1.

The cyclic PG structure is sufficiently small to allow it to cross the blood-brain barrier.

In addition, as shown in FIG. 2 the structure of the molecule is such that it is able to provide ligands for binding metal ions such as $Mg^{2+}$, $Ca^{2+}$, $Co^{2+}$ and the like and as such can act as a chelating agent.

The possible role of cPG as an agent is further supported by the companion break down product, glutamic acid.

Glutamic acid is known to be associated with brain disease. (Johnston, G. A. R. in Roberts P. J. et al Editors, Glutamate: Transmitter in the Central Nervous System, John Wiley & Sons, 1981, pp. 77-87).

As used herein, a cPG compound is a compound with biological activity similar or identical to the biological activity of cPG; cPG compounds comprise cPG, biologically active cPG analogues, biologically active cPG mimetics, and compounds that increase the concentration of cPG and cPG analogues in a mammal. cPG compounds include cPG agonist molecules such as truncated portions of IGF-I compounds as well as other chemical and biological analogues and mimetics.

As used herein, "cPG analogue" is any analogue of cPG, naturally occurring analogue of cPG, or any variants thereof, which are capable of effectively binding to mGluR receptors in the CNS and of promoting an equivalent neuroprotective effect on CNS nerve cells.

The term "cPG agonist molecules" includes peptide fragments and truncated portions of longer IGF-I compounds as well as other chemical and biological analogues and mimetics. cPG compounds can be used in the treatment of mammals, suffering from neutral injury or disease. In particular the cPG compounds can be used to treat human patients, suffering from neural injury or disease. Still more generally, the compositions and methods of the invention find use in the treatment of mammals, such as human patients, suffering from nerve damage or potential apoptotic and/or necrotic cell death, due to injuries and diseases such as septic shock, ischemia, administration of cytokines, overexpression of cytokines, ulcers, gastritis, ulcerative colitis, Crohn's disease, diabetes, rheumatoid arthritis, asthma, Alzheimer's disease, Parkinson's disease, multiple sclerosis, stroke, cirrhosis, allograft rejection, transplant rejection, encephalomyelitis, meningitis, pancreatitis, peritonitis, vasculitis, lymphocytic choriomeningitis, glomerulonephritis, uveitis, glaucoma, blepharitis, chalazion, allergic eye disease, corneal ulcer, keratitis, cataract, retinal disorders, age-related macular degeneration, optic neuritis ileitis, inflammation induced by overproduction of inflammatory cytokines, hemorrhagic shock, anaphylactic shock, burn, infection leading to the overproduction of inflammatory cytokines induced by bacteria, virus, fungus, and parasites, hemodialysis, chronic fatigue syndrome, stroke, cancers, cardiovascular diseases associated with overproduction of inflammatory cytokines, heart disease, cardiopulmonary bypass, ischemic/reperfusion injury, ischemic/reperfusion associated with overproduction of inflammatory cytokines, toxic shock syndrome, adult respiratory distress syndrome, cachexia, myocarditis, autoimmune disorders, eczema, psoriasis, heart failure, dermatitis, urticaria, cerebral ischemia, systemic lupus erythematosis, AIDS, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Huntington's disease, epilepsy, gastrointestinal motility disorders, obesity, hyperphagia, neuroblastoma, malaria, hematologic cancers, myelofibrosis, lung injury, graft-versus-host disease, head injury, CNS trauma, hepatitis, renal failure, chronic hepatitis C, paraquat poisoning, transplant rejection and preservation, fertility enhancement, bacterial translocation, circulatory shock, traumatic shock, hemodialysis, hangover, and combinations of two or more thereof.

In addition, cPG may be used to treat mammals suffering from white matter insult as the result of acute brain injury, such as perinatal hypoxic-ischemic injury; or from chronic neural injury or neurodegenerative disease, such as multiple sclerosis, or from other demyelinating diseases and disorders including inflammatory involvement, such as acute disseminated encephalomyelitis, optic neuritis, transverse myelitis, Devic's disease, the leucodystrophies; non-inflammatory involvement; progressive multifocal leukoencephalopathy, central pontine myelinolysis. Patients suffering from such diseases or injuries will benefit greatly by a treatment protocol able to initiate re-myelination.

The present invention has application in the induction of myelin production following insult in the form of trauma, toxin exposure, asphyxia or hypoxia-ischemia, and has application in the treatment or prevention of apoptosis in response to injury or disease in the form of cancers, viral infections, autoimmune diseases, neurological diseases and injuries and cardiovascular diseases.

cPG treatment may be given before (as well as alter) an injury—as for example before elective surgery. Examples of relevant elective procedures include neural surgery, in which retraction of lobes of the brain may lead to cerebral oedema, or heart operations, such as valve replacement, in which inevitable small emboli are said to lead to detectable impairment of brain function in some 75% of cases.

Pharmacology and Utility cPG can act as an anti-necrotic and anti-apoptotic in a process of cell death. Its anti-apoptotic and anti-necrotic activity in vivo can be measured by cell counts. cPG can also be measured in vitro. (Gudasheva T. A. et al. FEBS Letters, Vol. 391, Issues 1-2, Aug. 5, 1996, pp. 149-152). CNS damage may for example be measured clinically by the degree of permanent neurological deficit cognitive function, and/or propensity to seizure disorders. (Rakic L. J et al, in Rakic L. J et al Peptide and Amino Acid Transport Mechanisms in The Central Nervous System, 1988, The MacMillan Press Ltd. (London) pp. 167-181).

Pharmaceutical Compositions and Administration

CPG itself is used to prevent or treat cell damage and death and the induction of myelin production. Usually this is effected through the direct administration of cGP to the patient. If desired, a combination of the cPG compounds and its analogues can be administered in a pharmaceutically acceptable composition.

Those skilled in the art will appreciate there is no intention on the part of the applicants to exclude administration of other forms of cPG. By way of example, the effective amount of cPG in the CNS can be increased by administration of a pro-drug from of cPG, which comprises cPG and a carrier, cPG and the carrier being joined by a linkage which is susceptible to cleavage or digested within the patient. Any suitable linkage can be employed which will be cleaved or digested to release cPG following administration.

In addition, it is envisaged cPG levels may be increased through an implant that includes a cell line capable of expressing cPG in an active from within the CNS of the patient.

cPG can be administered as part of a medicament or pharmaceutical preparation. This can involve combining cPG with any pharmaceutically appropriate carrier, adjuvant or excipient. The selection of the carrier, adjuvant or excipient will of course usually be dependent upon the route of administration to be employed.

The administration route can vary widely. An advantage of cPG is that it can be administered peripherally. This means it need not be administered directly to the CNS of the patient in order to have effect in the CNS.

Any peripheral route known in the art can be employed. These can include parenteral routes for example injection into the peripheral circulation, subcutaneous, intraorbital, ophthalmic, intraspinal, intracisternal, topical, infusion (using e.g., controlled release devices or minipumps such as osmotic pumps or skin patches), implant, aerosol, inhalation, scarification, intraperitoneal, intracapsular, intramuscular, intranasal, oral, buccal, pulmonary, rectal or vaginal. The compositions can be formulated for parenteral administration to humans or other mammals in therapeutically effective amounts (e.g., amounts which eliminate or reduce the patient's pathological condition) to provide therapy for the neurological diseases described above.

Two of the preferred administration routes will be by subcutaneous injection (e.g., dissolved in 0.9% sodium chloride) or orally (in a capsule).

It will also be appreciated that on occasion it may desirable to directly administer IGF-I compounds to the CNS of the patient. Again, this can be achieved by any appropriate direct administration route. Examples include administration by lateral cerebroventricular injection or through a surgically inserted shunt into the lateral cerebroventricle of the brain of the patient.

The calculation of the effective amount of cPG compounds to be administered is within the skill of one of ordinary skill in the art, and will be routine to those persons skilled in the art. Needless to say, the final amount to be administered will be dependent upon the route of administration and upon the nature of the neurological disorder or condition that is to be treated. Preferably the cPG compound will be administered at between about 1 µg to 100 mg of cPG compound per 100 g of body weight where the dose is administered centrally. A suitable dosage for administration of cPG may be, for example, at between 0.1 mg to about 10 mg per 100 g of body weight, or at between about 1 mg to about 5 mg per 100 g body weight.

For inclusion in a medicament, cPG compounds can be obtained from a suitable commercial source such as Bachem AG of Bubendorf, Switzerland. Alternatively, cPG, cPG analogues and cPG mimetics can be directly synthesized by conventional methods such as the stepwise solid phase synthesis method of Merryfield et a!., 1963. Alternatively synthesis can involve in the use of commercially available peptide synthesizers such as the Applied Biosystems model 430A.

As a general proposition, the total pharmaceutically effective amount of the cPG agonist compound administered parenterally per dose will be in a range that can be measured by a dose response curve. One can administer increasing amounts of the cPG agonist compound to the patient and check the serum levels of the patient for cPG. The amount of cPG agonist to be employed can be calculated on a molar basis based on these serum levels of cPG.

Specifically, one method for determining appropriate dosing of the compound entails measuring cPG levels in a biological fluid such as a body or blood fluid. Measuring such levels can be done by any means, including RIA and ELISA. After measuring cPG levels, the fluid is contacted with the compound using single or multiple doses. After this contacting step, the cPG levels are re-measured in the fluid. If the fluid cPG levels have fallen by an amount sufficient to produce the desired efficacy for which the molecule is to be administered, then the dose of the molecule can be adjusted to produce maximal efficacy. This method can be carried out in vitro or in vivo. Preferably, this method is carried out in vivo, i.e., after the fluid is extracted from a mammal and the cPG levels measured, the compound herein is administered to the mammal using single or multiple doses (that is, the contacting step is achieved by administration to a mammal) and then the cPG levels are remeasured from fluid extracted from the mammal.

The compound may also be suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919; EP 58,481), copolymers of L-glutamic acid and gamma-ethyl-L-glutamate (Sidman et al., 1983), poly(2-hydroxyethyl methacrylate) (Langer et al, 1981), ethylene vinyl acetate (Langer et al., supra), or poly-D-(−)-3-hydroxybutyric acid (EP 133,988). Sustained-release compositions also include a liposomally entrapped compound. Liposomes containing the compound are prepared by methods known per se: DE Patent 3,218,121; Epstein et al., 1985; Hwang et al., 1980; EP Patent 52,322; EP Patent 36,676; EP Patent 88,046; EP Patent 143,949; EP Patent 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol. percent cholesterol, the selected proportion being adjusted for the most efficacious therapy.

PEGylated peptides having a longer life can also be employed, based on, e.g., the conjugate technology described in WO 95/32003 published Nov. 30, 1995.

If parenteral administration is preferred, the compound is formulated generally by mixing each at the desired concentration, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation.

Generally, the formulations are prepared by contacting the compound with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate may also be used.

The carrier may additionally contain additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counterions such as sodium; non-ionic surfactants such as polysorbates, poloxamers, or polyethylene glycol (PEG); and/or neutral salts, e.g., NaCl, KCl, $MgCl_2$, $CaCl_2$, etc.

The cPG compound is typically formulated in such vehicles at a pH of between about 5.5 to 8. Typical adjuvants which may be incorporated into tablets, capsules, and the like are a binder such as acacia, corn starch, or gelatin; an excipient such as microcrystalline cellulose; a disintegrating agent like corn starch or alginic acid; a lubricant such as magnesium stearate; a sweetening agent such as sucrose or lactose; a flavoring agent such as peppermint, wintergreen, or cherry. When the dosage form is a capsule, in addition to the above materials, it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a coloring agent, and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants, and the like can be incorporated according to accepted pharmaceutical practice.

The compound to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

The compound ordinarily will be stored in unit or multi-dose containers, for example, sealed glass ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Combination therapy with the cPG agonist compound herein and one or more other appropriate reagents that increase total cPG in the blood or enhance the effect of the cPG agonist is also contemplated. These reagents generally allow the cPG agonist compound herein to release the generated cPG.

In addition, it is envisaged using gene therapy for treating a mammal, using nucleic acid encoding the cPG agonist compound, if it is a peptide. Generally, gene therapy is used to increase (or overexpress) cPG levels in the mammal. Nucleic acids, which encode the cPG agonist peptide can be used for this purpose. Once the amino acid sequence is known, one can generate several nucleic acid molecules using the degeneracy of the genetic code, and select which to use for gene therapy.

There are two major approaches to getting the nucleic acid (optionally contained in a vector) into the patient's cells for purposes of gene therapy: in vivo and ex vivo. For in vivo delivery, the nucleic acid is injected directly into the patient, usually at the site where the cPG agonist compound is required. For ex vivo treatment, the patient's cells are removed, the nucleic acid is introduced into these isolated cells, and the modified cells are administered to the patient either directly or, for example, encapsulated within porous membranes which are implanted into the patient. See, e.g., U.S. Pat. Nos. 4,892,538 and 5,283,187.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell-surface membrane protein or the target cell, a ligand for a receptor on the target cell, etc. Where liposomes are employed, proteins which bind to a cell-surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., 1987; Wagner et al., 1990). For review of the currently known gene marking and gene therapy protocols, see Anderson 1992. See also WO 93/25673 and the references cited therein.

Kits are also contemplated for this invention. A typical kit would comprise a container, preferably a vial, for the cPG agonist compound formulation comprising cPG agonist compound in a pharmaceutically acceptable buffer and instructions, such as a product insert or label, directing the user to utilize the pharmaceutical formulation.

EXAMPLES

Experiment 1

Cyclic PG prevents glutamate induced neuronal death in vitro in a dose related manner.

Materials and Methods:

Cerebellar Cell Culture Preparing and Coating of Cover Slips

Ten coverslips were placed into a large petri dish and washed in 70% alcohol for 5 minutes, then washed with Millipore $H_2O$. The coverslips were air dried, then coated with Poly-D-Lysine (1 mg/ml stock solution in PBS, 90-100 µl) and incubated for 2 hours at 34 C.

Extraction

Postnatal day 4 Wistar rats were used for the study. Rats were placed in ice for 1 minute, the heads were decapitated and the cerebellum removed on ice. Cerebellum tissue was placed in 1 ml of 0.65% glucose supplemented PBS (10 µl 65% stock D (+)glucose/1 ml PBS) in a large petri dish, chopped up into smaller sections and triturate with a 1 ml insulin syringe via a 23 G (0.4 mm) needle, and then squirted back into the glucose solution on the large petri dish. The tissue was sieved through (125 µm pore size gaze) and centrifuged (2 minutes at 60 g) two times for a medium exchange into serum-free BSA-supplemented START V medium (Biochrom). The second centrifugation step was done with 1 ml of START V medium. The microexplants were reconstituted into 500 µl of START V medium and put on ice Cultivation and Fixation of Cerebellar Cells Two hours after PDL-coating, the slides were washed with Millipore $H_2O$ and air dried. Each slide was placed into a small 35 mm petri dish and 40 µl of START V/cell suspension added. The tissue was incubated for 2 hours at 34 C (settlement period). START V-medium (1 ml) was then added to the petri dish and cultivated at 34 C/5% CO2/100% humidity for 48 hours. Cells were rinsed in PBS and then fixed for 2-3 minutes in increasing concentrations of paraformaldehyde (500 µl of 0.4% PFA was applied; then 1.2% PFA; then 3% PFA and finally 4% PFA—all fixation solutions contain 0.2% glutardialdehyde). Finally, the microexplants were rinsed in PBS.

Drug Application

10 µl of toxin (L-glutamate-100 mM in Millipore water) was applied simultaneously with cPG (from bachem, 10 mM stock prepared in PBS and diluted to final concentrations between 1-100 nM) for Study 1. A delay in administration of cPG at 6 hours after glutamate treatment was performed for Study 2.

Figure 3:
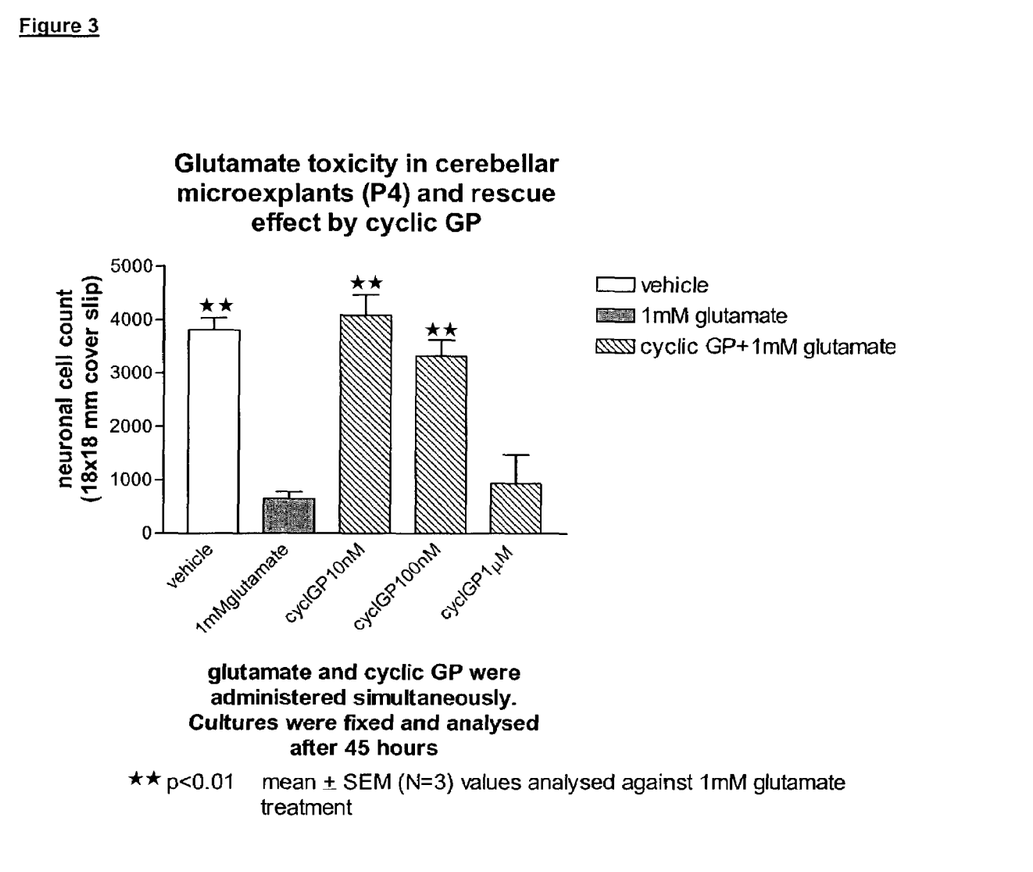
FIG. 3 illustrates in graphic form Glutamate toxicity in cerebellar microexplants (P4) and rescue effect by cyclic GP.

Result:

Study 1: Glutamate treatment resulted in 85% loss of cerebellum neurons. Cyclic PG significantly reduced the glutamate induced neuronal death in a dose response manner when administered simultaneously with glutamate (FIG. 3). The treatments with lower doses of cPG (10-100 nM) showed significant recovery from glutamate-induced neurotoxicity.

Figure 4:
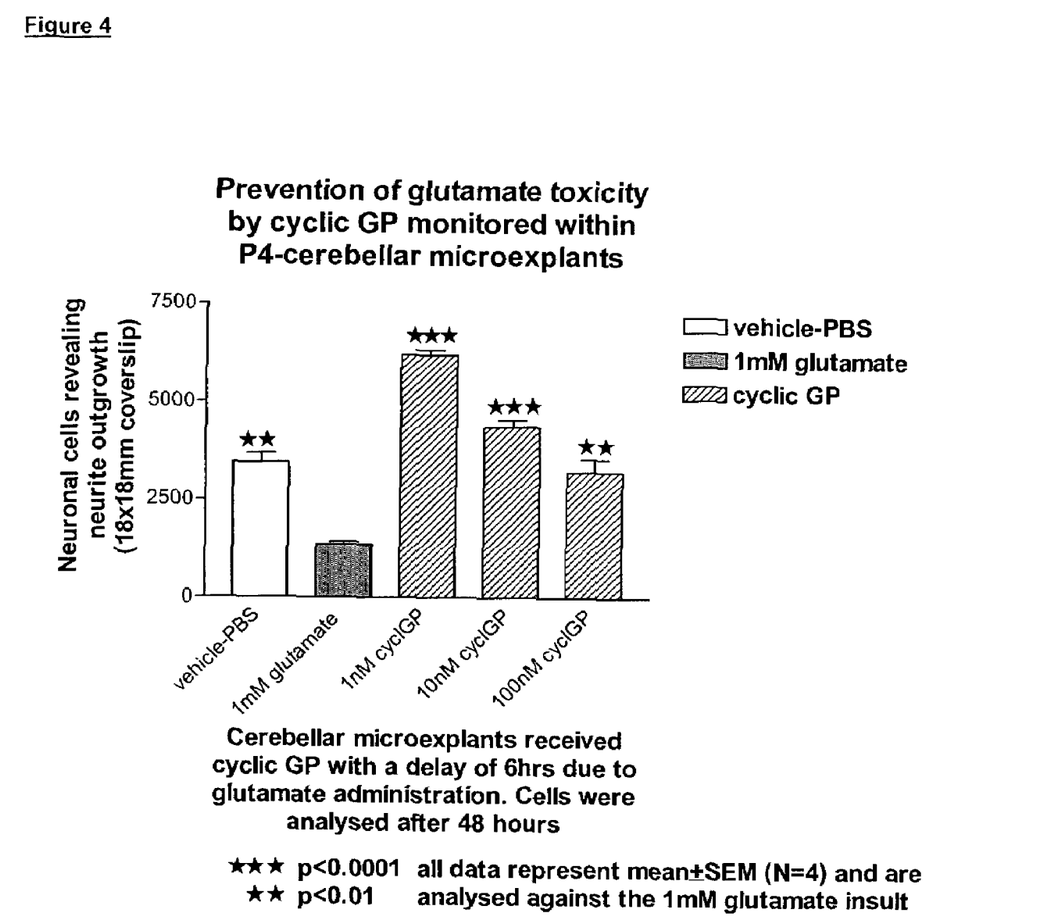
FIG. 4 illustrates in graphic form prevention of glutamate toxicity by cyclic GP monitored within P4-cerebellar microexplants.

Study 2: Cyclic PG showed a significantly recovery from glutamate induced neurotoxicity in a dose range of 1-100 nM when given 6 hours after the glutamate treatment compared to the vehicle treated group (FIG. 4).

A further lower dose of cPG also showed a significant increase in neuron number compared to the normal control group, suggest a role for cPG in neuronal proliferation and differentiation.

Conclusions

Excessive glutamate can cause neuronal excitotoxicity by active NMDA receptors. Cyclic PG completely prevented the glutamate-induced neurotoxicity, when given either immediately or 6 hours after the glutamate treatment by acting as a direct or indirect NMDA antagonist. Given that cPG can agonise mGlu2/3 receptor, which can inhibit NMDA activity. GPE, the pre-hormone for cPG has been shown to be partial NMDA receptor agonist in promoting pCREB, probably due to its antagonistic effect on mGlu2/3 receptors. CPG may be involved in preventing neurons undergoing apoptosis because cPG appeared to be still effective as a delayed treatment, and promoted the neuronal proliferation.

Experiment 2

Effects of cPG after 6-OHDA induced nigral-striatal lesion.

Materials and Methods

Twenty male Wistar rats (280-310 g) were used. After exposing the skull, 6-OHDA (8 µg in a base of 2 µl 0.9% saline containing 1% ascorbic acid) was administered into the right medial forebrain bundle (MFB) using co-ordinates AP +4.7 mm, R 1.6 mmv-8 mm under 3% halothane anaesthesia. 6-OHDA was injected through a 25 G needle connected via a polyethylene catheter to a 100 µl Hamilton syringe. The 6-OHDA was infused by a microdialysis infusion pump at a rate of 0.5 µl/min. The needle was left in the brain for a further 3 minutes before being slowly withdrawn. The skin was sutured with 2.0 silk and the rats were allowed to recover from anaesthesia. The rats were housed in a holding room with free access to food and water at all times except during behavioural testing.

Cyclic PG was dissolved in saline. Four different doses of cPG (0, 0.1 0.5 1 mg/kg, Bachem) were administered intraperitoneally 2 h post lesion.

At 7 days post-lesion, rats were injected with 0.1 mg/kg apomorphine and the number of contralateral rotations/hour was recorded and calculated using a computerised Rotameter (St Diego Instruments). Experimenter was blinded from the treatment groups.

Figure 5:
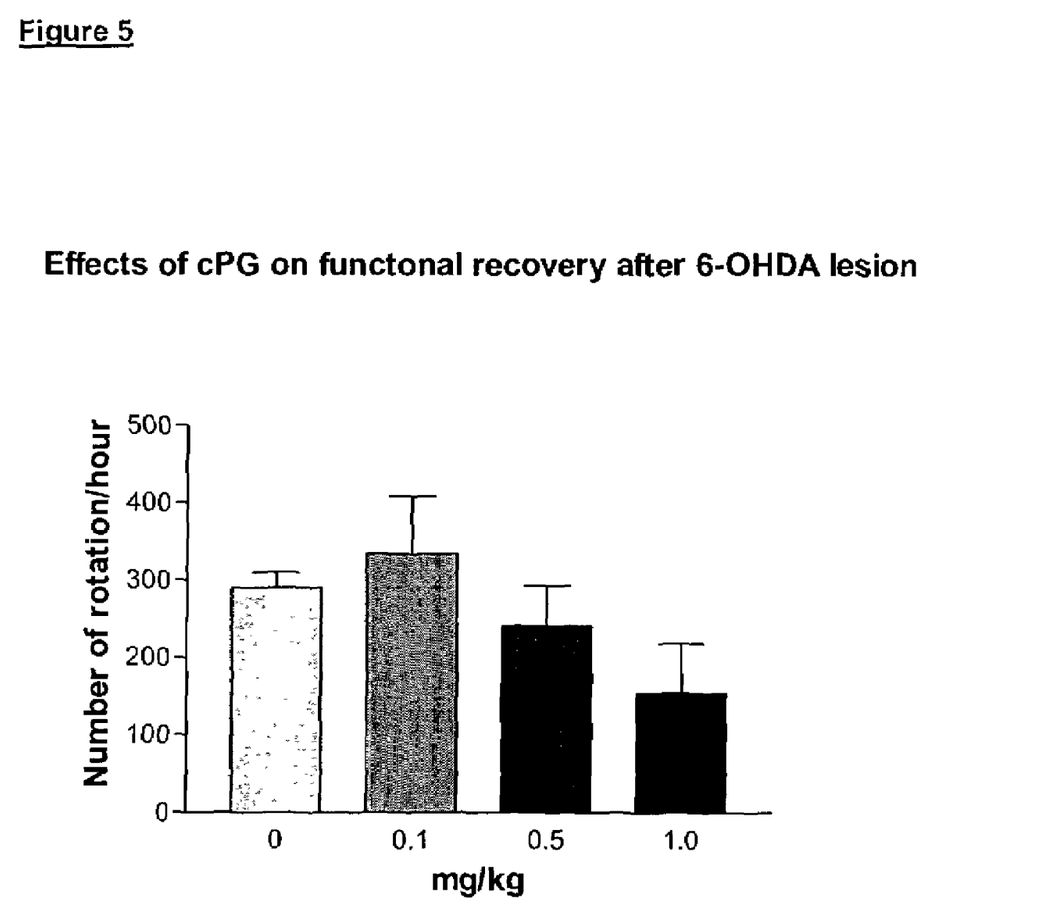
FIG. 5 illustrates in graphic form effects of cPG on functional recovery after 6-OHDA lesion

Result:

The group treated with 1 mg cPG (n=5, 154±64.1) showed a trend toward a reduction in the number of rotations compared to the vehicle treated group (n=5, 290.08±18.9) indicating a role for cPG in improving functional recovery in 6-OHDA induced nigrostriatal injury. (FIG. 5)

Conclusions

Cyclic PG improved the functional recovery after 6-OHDA induced nigral-striatal lesions in a dose related manner.

The highest dose tested (1 mg/kg) reduced functional deficit (apomorphine induced rotations) by 47% (ns). This data suggested cPG has potential as a treatment for Parkinson's disease.

ADVANTAGES

Some advantages offered by the present invention, especially over IGF-I and the GPE include:

The active ingredients are easy to synthesise either in vitro or by other means such as recombinant techniques.

The dipeptide as a small molecule can diffuse readily through the body and between compartments (e.g. the blood-brain barrier, and mucous membranes), aiding in the choice of methods for its administration and its ability to reach sites where injury has occurred.

cPG is a very stable molecule and is unlikely to present a challenge to the immune system, so it may be administered over extended periods and it may be administered prophylactically.

With their antagonistic and agonistic effects, GPE/cPG, the present invention provides a novel therapeutic method for preventing brain injury and degenerative diseases by regulating mGluRs particularly ⅔ leading to long-term benefits of brain recovery.

With a role in regulating IGF-1 induction, cPG will provide further neuroprotection with less potential for growth side-effects.

While various embodiments of the present invention have been described above, it should be understood that they have been presented by way of examples only, and not limitation. It will be understood by those skilled in the art that various changes in form and detail may be made therein without departing from the spirit and scope of the present invention as defined in the appended claims. Thus, the breadth and scope of the present invention should not be limited by any of the abovedescribed exemplary embodiments, but should be defined in accordance with the following claims and their equivalents.

All publication, including patent documents and scientific articles, referred to in this application, including any bibliography, are incorporated by reference in their entirety for all purposes to the same extent as if each individual publication were individually incorporated by reference. All headings are for the convenience of the reader and should not be used to limit the meaning of the text that follows the heading, unless so specified.

What is claimed is:

1. A method of protecting neurons and glia otherwise destined to die as a result of an insult from injury or disease, comprising the step of:
   administering cyclic Prolyl Glycine in an amount sufficient to prevent the neurons and glia from dying.

2. The method of claim 1, wherein the dosage range of said cyclic Prolyl Glycine is from about 1 µg to about 150 mg per kg of body weight.

3. The method of claim 1, wherein said administration is in the form of a pharmaceutical composition including pharmaceutically acceptable carrier thereof.

4. The method of claim 1, wherein said administration is directly to the brain or cerebrospinal fluid.

5. The method of claim 1, wherein said administration is in combination with artificial cerebrospinal fluid.

6. The method of claim 1, wherein said administration is through one or more routes selected from the group consisting intravenous, oral, rectal, nasal, subcutaneous, inhalation, intraperitoneal, and intramuscular.

7. The method of claim 1, wherein said administration is combined with one or more neuroprotective agent, a) said neuroprotective agent is selected from the group consisting of insulin-like growth factor-I (IGF-I), insulin growth-like factor-II (IGF-II), transforming growth factor-$\beta$1, activin, growth hormone, nerve growth factor, growth hormone binding protein, IGF-binding proteins (especially IGFBP-), basic fibroblast growth factor, acidic fibroblast growth factor, the hst/Kfgk gene product, fibroblast growth factor 3 (FGF-3), fibroblast growth factor 4 (FGF-4), fibroblast growth factor 6 (FGF-6), keratinocyte growth factor, androgen-induced growth factor, int-2, fibroblast growth factor homologous factor-1 (FHF-1), fibroblast growth factor homologous factor-2 (FHF-2), fibroblast growth factor homologous factor-3 (FHF-3), fibroblast growth factor homologous factor-4 (FHF-4), karatinocyte growth factor 2, glial-activating factor, fibroblast growth factor-10 (FGF-10) and fibroblast growth factor-16 (FGF-16), ciliary neurotrophic factor, brain derived growth factor, neurotrophin 3, neurotrophin 4, bone morphogenetic protein 2 (BMP-2), glial-cell line derived neurotrophic factor, activity-dependant neurotrophic factor, cytokine leukemia, inhibiting factor, oncostatin M, interleukin, $\beta$, $\alpha$, $\chi$, or consensus interferon, tumor necrosis factor-$\alpha$ (TNF-$\alpha$), clomethiazole; kynurenic acid, Semax, FK506 (tacrolimus), L-threo-1-pheyl-2-decanoylamino-3-morpholino-1-propanol, andrenocorticotropin-(4-9_analogue (ORG 2766)) and dizolcipine (MK-801), and selegiline; or b) said neuroprotective agent is a glutamate antagonist selected from the group consisting of NPS1506, GV1505260, MK-801, and GV150526; or c) said neuroprotective agent is an alpha-amino-3-hydroxy-5-methyl 4-isoxazole proprionic acid (AMPA) antagonist selected from the group consisting of 2,3-dihydroxy-6-nitro-7-sulfamoylbenzo(f)-quinoxaline (NBQX), LY303070 and LY300164; or d) said neuroprotective agent is an anti-inflammatory agent directed against mucosal vascular addressing cell adhesion molecular 1 (MAdCAM-1) and/or integrin $\alpha$4 receptors ($\alpha$4$\beta$1 and $\alpha$4$\beta$7) or anti-MAdCAM-1mAb MECA-367 (ATCC accession no. HB-9478); or e) said neuroprotective agent is a combination of two or more agents provided in a) through d).

8. The method of claim 1, wherein said administration is combined with one or more anti-inflammatory agents selected from the group consisting of anti-integrin alpha 4 subunit reagents, anti-integrin beta 7 subunit reagents, anti-integrin beta 2 subunit reagents, anti-integrin alpha L subunit reagents, anti-mucosal vascular addressing cell adhesion molecular 1 (anti-MAdCAM-1), anti-vascular cell adhesion molecule 1 (anti-VCAM-1) reagents, and anti-intercellular adhesion molecule (anti-ICAM) reagents.

* * * * *